US008628479B2

(12) United States Patent
Lomask et al.

(10) Patent No.: US 8,628,479 B2
(45) Date of Patent: Jan. 14, 2014

(54) PLETHYSMOGRAPH WITH ANIMAL RESTRAINT

(75) Inventors: Joseph Lomask, Wilmington, NC (US); Yuval Shemesh, Wilmington, NC (US); Richard A. Shafer, Wilmington, NC (US); Chau Hong Le, Wilmington, NC (US); Hai dang Nguyen, Wilmington, NC (US)

(73) Assignee: Buxco Electronics, Inc., Sharon, CT (US)

(*) Notice: Subject to any disclaimer, the term of this patent is extended or adjusted under 35 U.S.C. 154(b) by 1119 days.

(21) Appl. No.: 12/589,332

(22) Filed: Oct. 22, 2009

(65) Prior Publication Data

US 2011/0098581 A1 Apr. 28, 2011

(51) Int. Cl.
*A61B 5/08* (2006.01)

(52) U.S. Cl.
USPC .......................................... 600/529

(58) Field of Classification Search
USPC .......................................... 600/529
See application file for complete search history.

(56) References Cited

U.S. PATENT DOCUMENTS

| | | |
|---|---|---|
| 3,625,185 A | 12/1971 | Kester |
| 3,739,751 A | 6/1973 | Mohr et al. |
| 3,976,053 A | 8/1976 | Reininghaus |
| 4,332,244 A | 6/1982 | Levy et al. |
| 4,520,808 A | 6/1985 | LaBauve |
| 4,582,055 A | 4/1986 | McDougal et al. |
| H145 H | 10/1986 | James |
| 4,660,572 A | 4/1987 | Maruyama et al. |
| 4,721,060 A | 1/1988 | Cannon et al. |
| 4,841,982 A * | 6/1989 | Nikiforov et al. ............. 600/529 |
| 5,099,792 A | 3/1992 | Cannon et al. |
| 5,297,502 A | 3/1994 | Jaeger |
| 5,320,069 A | 6/1994 | Anderson, Jr. et al. |
| 5,927,234 A | 7/1999 | Siegel |
| 6,651,587 B1 | 11/2003 | DeFord et al. |
| 7,071,194 B2 | 7/2006 | Teng |
| 7,377,276 B2 | 5/2008 | Roy et al. |
| 2004/0254489 A1 * | 12/2004 | Lomask ...................... 600/529 |
| 2006/0278218 A1 | 12/2006 | Hoffman |
| 2008/0168948 A1 | 7/2008 | Truitt et al. |

OTHER PUBLICATIONS

Flandre et al. "Effect of somatic growth, strain, and sex on double-chamber plethysmographic respiratory function values in healthy mice". J Appl Physiol 94: 1129-1136, 2003.*

* cited by examiner

*Primary Examiner* — Patricia Mallari
*Assistant Examiner* — Christian Jang
(74) *Attorney, Agent, or Firm* — MacCord Mason PLLC

(57) ABSTRACT

A plethysmograph is described that includes a test chamber having an opening; a sealing member including an annular flexible seal to receive at least a part of the head of the test animal mounted across the opening whereby the animal breathes air outside the test chamber, while the animal's body is within the test chamber; and a restraining member attachable to the sealing member, the restraining member including a clamp positionable behind the test animal's head, to prevent the animal from withdrawing its head from the restraining member. The animal is positioned in the restraining member and the sealing member is attached to the restraining member before insertion of the animal and assembly into the test chamber, avoiding previous difficulties in simultaneously placing an animal into the chamber while inserting the animal's nose into the seal. The plethysmograph also eliminates the necessity for a plunger to prevent rearward movement of the animal.

14 Claims, 3 Drawing Sheets

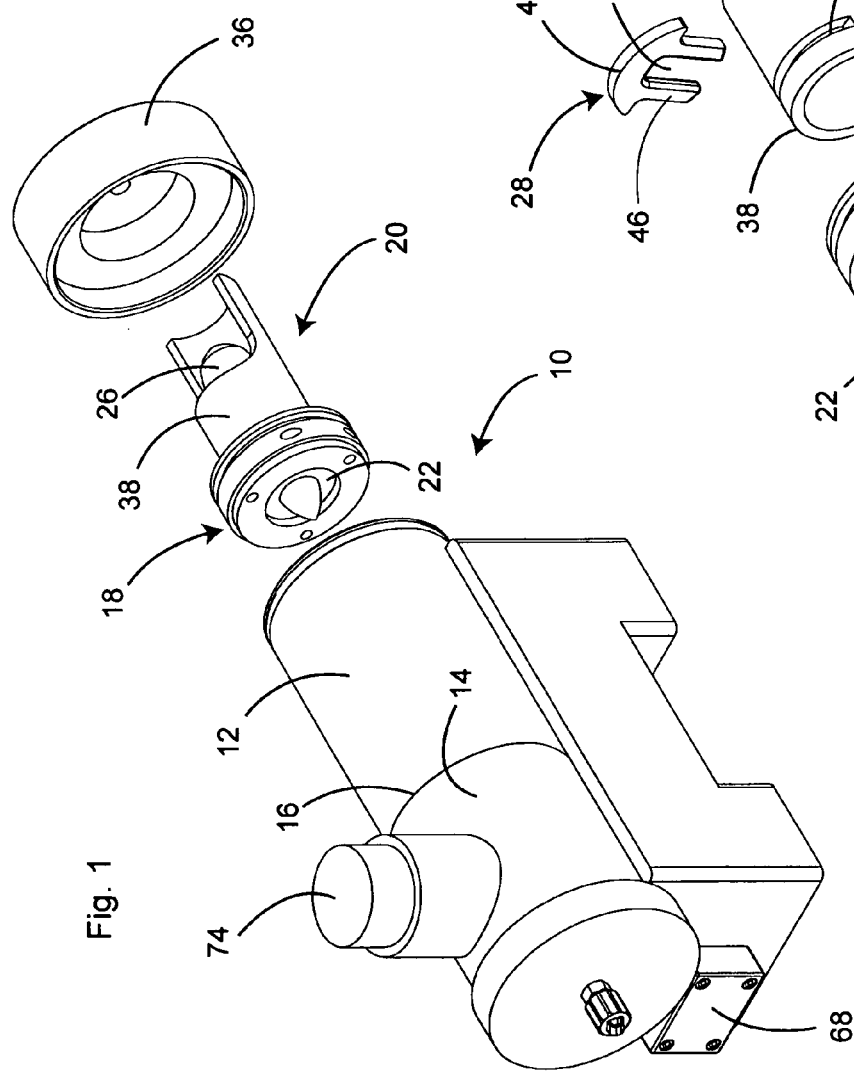
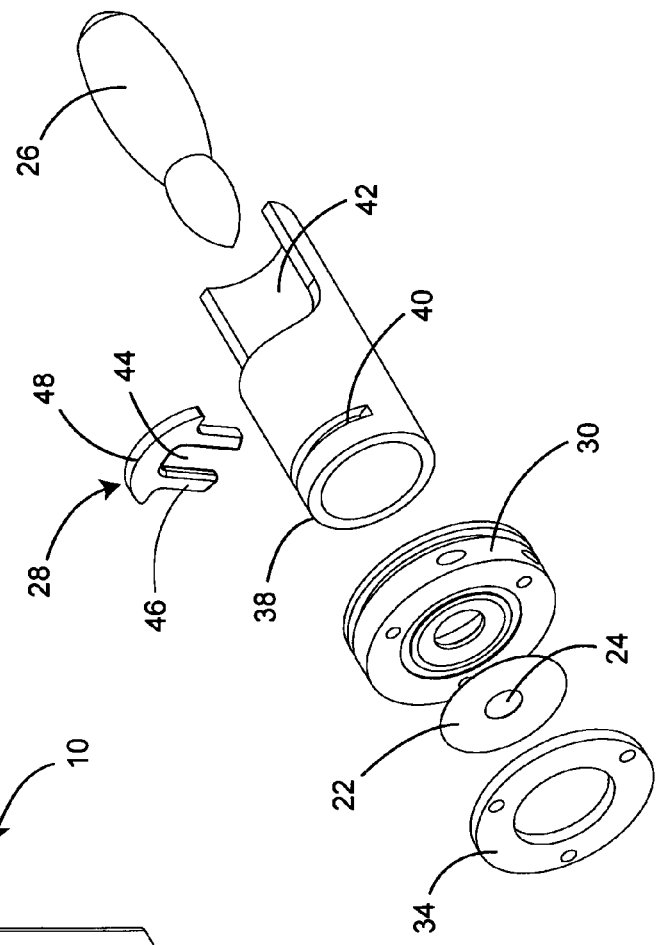

PLETHYSMOGRAPH WITH ANIMAL RESTRAINT

BACKGROUND OF THE INVENTION (1) Field of the Invention

The present invention relates to plethysmographs used for measuring changes in air volume, such as in non-invasive pulmonary testing of small animals, and in particular to plethysmographs that include an animal restraint to facilitate attachment of a barrier seal and insertion of the test animal into the plethysmograph chamber.

(2) Description of the Prior Art

Plethysmographs are used in research to collect data relating to changes in air pressure within a test chamber. An example of such data is pulmonary data from small animals, such as mice. Most plethysmographs are comprised of a test chamber to enclose the test subject, and a transducer port connected via tubing to a differential pressure transducer. As changes to the air volume within the test chamber occur, pressure variations are recorded by the transducer, which normally displays the recorded data in numerical form or as a graph.

Plethysmographs are commonly used to measure the pulmonary activities of mice and other small animals that are completely or substantially enclosed within the test chamber. As the test animal inhales or exhales, the changes in air volume results in pressure variations that are recorded by the transducer, which normally displays the recorded data in numerical form or as a graph.

The plethysmograph may also include a reference chamber to partially reduce the affect of background noise resulting from variations in air pressure entering the test chamber, with the reference chamber having a port connected to the transducer. The transducer simultaneously measures variations in air pressures within the test and reference chambers, and subtracts the reference chamber measurements from the test chamber measurements. As a result, the net pressure variations are essentially attributable to the respiration patterns of the test animal. Preferably, the test and reference chamber pneumotachs through which the air enters the chambers are close to each other to minimize variations in exterior air patterns.

In one type of plethysmograph, known as a dual-chamber plethysmograph, two chambers, the nasal and thoracic chambers, are attached end-to-end at their respective attachment openings, with a barrier seal being fitted between the chambers to prevent passage of air between the chambers. The seal, sometimes referred to as a neck seal or nose seal, includes a central opening sized to receive at least part of the test animal's head including the nose, i.e., only the animal's nose up to all of the animal's head may be inserted through the seal opening. As used herein, a statement to the effect that the "head" of the test animal is inserted through the seal opening should be understood to mean that at least the nose is inserted and includes insertion of only a part of the animal's head through the opening, as well as the entire head of the test animal. The thoracic chamber includes a test animal insertion opening opposite the seal, and a may include a pusher or plunger insertable through the insertion opening.

In use, the test animal is inserted into the chamber and, if necessary, pushed forward with the plunger so that the animal's head or a part thereof projects through the seal opening. The animal then breathes air within the nasal chamber, while it body is in the thoracic chamber. The thoracic expansion or changes in volume of the animal's body within the thoracic chamber due to inspiration and expiration can then be measured as the animal breathes. Simultaneously, as the animal breathes, air is drawn out of and pushed into the nasal chamber, and the nasal respiratory flow is measured by the nasal chamber. By measuring the two flows simultaneously, specific airway resistance can be derived, as well as other useful measures of pulmonary mechanics. Since specific airway resistance is a principal measure commonly sought using this technique, it is desirable to make a very good seal which does not introduce any resistance of its own.

Placement of a neck seal or nose seal onto a conscious animal while simultaneously restraining the animal within the test chamber can be very challenging to the operator. Therefore, there is a need for a plethysmograph designed to facilitate the insertion of the animal into the plethysmograph and proper seating of the seal around the animal's head.

SUMMARY OF THE INVENTION

Generally, the present invention relates to an improved plethysmograph which includes, in addition to the normal plethysmograph structure, a restraining member to secure the test animal with the barrier seal positioned onto the test animal before the test animal is placed into the plethysmograph chamber.

While the invention will be described herein in the context of a dual-chamber plethysmograph, it will be apparent that the invention is applicable to other types of plethysmographs where an animal's body is isolated from the animal's head or portion thereof, permitting measurement of nasal and/or thoracic changes in air volume. Therefore, in its broadest application, the present invention is comprised of a test chamber, the term referring to either a nasal or thoracic chamber, having a sealing member opening; a sealing member mountable across the opening, the sealing member including a seal with an opening to receive the head of the test animal whereby the animal breathes air on one side of the seal, while the animal's body is isolated on the other side of the seal; and a restraining member attachable to the sealing member, the restraining member including a clamp positionable behind the test animal's head, thereby preventing the animal from withdrawing its head from the restraining member, the animal being positioned in the restraining member and the sealing member being attached to the restraining member before mounting of the sealing member across the test chamber opening.

For example, where the test chamber is a thoracic chamber with an opening, the animal held by the restraining member is inserted into the thoracic chamber with the sealing member blocking airflow through the sealing member opening. When in position, the animal's body is within the thoracic chamber, with the animal's head, or at least the animal's nose, being outside the thoracic chamber so that the animal breathes air outside the thoracic chamber. In one application, multiple plethysmographs may be used, with the heads of the test animals being inserted into a common column containing an aerosol or nebulized compound. Changes in thoracic volume can then be measured with a pressure transducer.

Similarly, where the test chamber is a nasal chamber with an opening, the head of the animal, with the animal held by the restraining member, is inserted into the nasal chamber with the sealing member blocking airflow through the sealing member opening. When in position, the animal's body is supported outside the nasal chamber by the restraining member with the animal's head, or at least the animal's nose, being inside the nasal chamber so that the animal breathes air inside the nasal chamber. Changes in nasal volume can then be measured with a pressure transducer.

With specific reference to the dual-chamber plethysmograph embodiment, the present invention is comprised of a first chamber having a first attachment opening, a second chamber having a second attachment opening attachable to the first attachment opening at an interface, a sealing member mountable between the first and second chambers to block the passage of air between the chambers, and a restraining member attachable to the sealing member, e.g., by sliding the sealing member onto one end of the restraining member.

The sealing member includes a barrier seal, preferably a flexible seal, with an opening to receive at least a part of the head of the test animal, whereby the animal breathes air in the second chamber, while the animal's body is within the first chamber. The restraining member includes a clamp positionable behind the test animal's head to prevent the animal from withdrawing its head from the restraining member.

Instead of being required to simultaneously restrain the animal into the test chamber while inserting the animal's head into the seal opening, the researcher inserts the animal's head into the restraining member and clamps the animal behind the head with the clamp, preventing the animal from withdrawing its head from the restraining member. The operator then fits the seal over the animal's head, securing the sealing member to the restraining member. Finally, the operator inserts the joined sealing and restraining members and the restrained animal into the test chamber, securing the sealing member across the test chamber opening.

Once in the chamber, the clamp is the only means required to prevent the animal from withdrawing its head from the seal opening. Specifically, there is no need to use the conventional pusher or plunger to prevent rearward movement of the animal. Therefore, the compression of the animal's lungs, and the resultant distortion of test results due to the affect on the animal's breathing patterns, heretofore experienced in using plungers in plethysmographs, is avoided.

The dual-chamber plethysmograph is preferably comprised of a cylindrical first chamber having an animal insertion end and a first attachment end opposite the insertion end, and a cylindrical second chamber having a second attachment end attachable to first attachment end. The sealing member is sized to block the passage of air between the chambers and includes an annular circular frame having an O-ring about its periphery, and a barrier seal, e.g., a latex seal, extending across center of the frame. The flexible seal has a central opening sized to receive the head of the test animal. The sealing member is attachable to one side of the restraining member. A closure is provided to cover the animal insertion end. Instead of the conventional plunger, the closure may be a simple cap friction fitted over the end of the cylinder.

The restraining member preferably includes a cylindrical wall section sized so that a peripheral flange at the rear of the sealing member frame can be frictionally fitted over the forward end of the wall section. In the preferred embodiments, the clamp is attachable within the wall section. The restraining member may also include a body platform to support the animal's body while the animal's head is held by the clamp.

Various clamping structures may be used to prevent the animal from withdrawing its head from the seal, the only essential requirements being that the clamp has an open position allowing the animal to insert its head into the restraining member and a closed position preventing the animal from withdrawing its head. In the closed position, the width of the clamp opening must be less than the width of the smallest dimension of the animal's head.

In one embodiment, the clamp is simply a plate having a U-shaped opening formed by two spaced tines. The spaced tines may be joined by a handle section. In use, the clamp is inserted through a slot in the restraining member, with the tines being positioned on opposite sides of the animal's neck.

In another embodiment, the clamp is comprised of a pair of spaced pivotal pins or rods positioned in a plane transverse to the longitudinal axis of the restraint opening. The pins are pivotal between an open position and one or more selected closed positions. The restraining member may include a latch to secure the pins in the selected closed positions. In use, the pins are placed in their open position until the animal's head is inserted. Then, the pins are pivoted toward each other until withdrawal of the animal's head is prevented.

In a third embodiment, a pair of spaced flexible cords extend across the restraint member opening. When is their open or relaxed state, the cords permit the animal to insert its head into the restraining member. However, when the cords are tightened, e.g., by pulling the cords taut with a cord lock, the spacing between the cords prevents the animal from withdrawing its head.

Each chamber includes a transducer port attachable to a transducer. In addition, the plethysmograph may also include a manifold with a common inlet for air flow via pneumotachs to the two chambers to minimize background noise, such as is described in commonly assigned U.S. Pat. No. 6,902,532, which is incorporated herein by reference.

BRIEF DESCRIPTION OF THE DRAWINGS

FIG. 1 is a perspective view of the plethysmograph and restraint.

FIG. 2 is a perspective exploded view of the restraint.

DETAILED DESCRIPTION OF THE INVENTION

In the following description, terms such as horizontal, upright, vertical, above, below, beneath, and the like, are used solely for the purpose of clarity in illustrating the invention, and should not be taken as words of limitation. The drawings are for the purpose of illustrating the invention and are not intended to be to scale.

Figure 3:
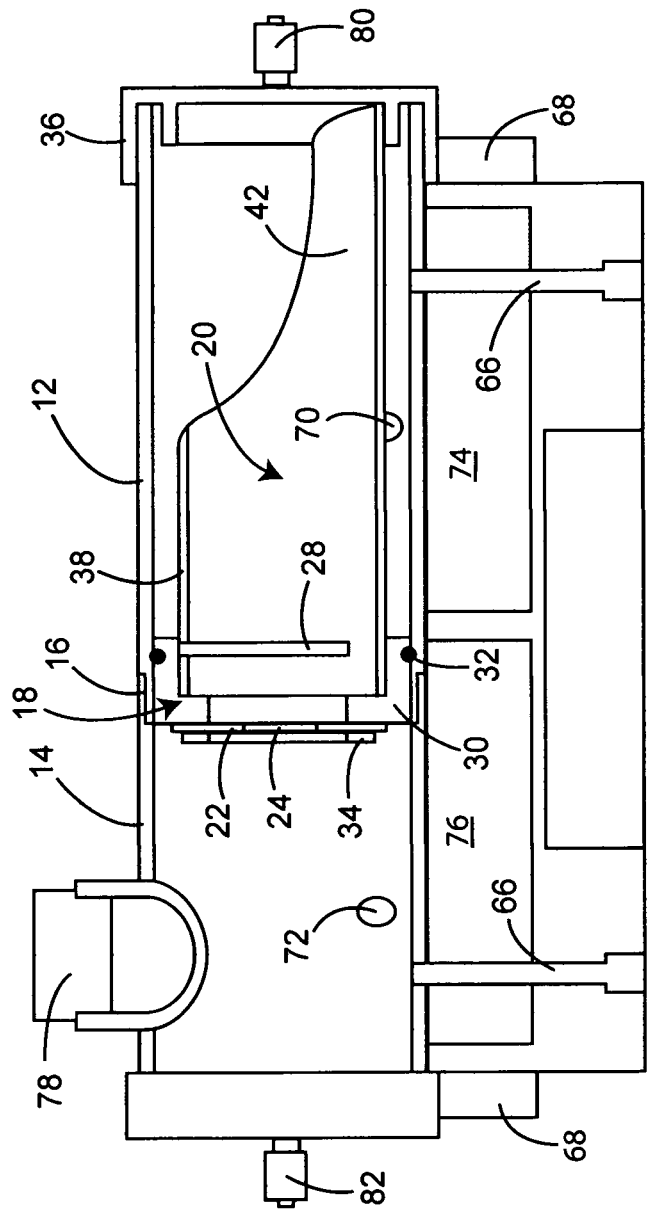
FIG. 3 is a sectional side view of the plethysmograph and restraining member.

As best illustrated in FIGS. 1 and 3, the plethysmograph, generally 10, is comprised of a first or thoracic chamber 12 and a second or nasal chamber 14 frictionally attached at an interface 16. A sealing member 18 is mounted between first and second chambers 12 and 14 to block the passage of air between the chambers, and a restraining member 20 is attached to one side of sealing member 18. Sealing member 18 includes a seal 22 with an opening 24 to receive the head of the test animal 26, e.g., a mouse, whereby animal 26 breathes air in second chamber 14, while the animal's body is within the first chamber 12. Restraining member 20 also includes a clamp 28 positionable behind the test animal's head to prevent animal 26 from withdrawing its head from restraining member 20.

Sealing member 18 is sized to block the passage of air between chambers 12 and 14, and includes an annular circular frame 30 having an O-ring 32 about its periphery. Flexible seal 22 extends across the center of frame 30 and is secured by ring 34. Closure 36 covers the animal insertion end of chamber 12 and can be configured to support the rear of restraining member 20.

Instead of being required to simultaneously restrain animal 26 in test chamber 12 while inserting the animal's head into seal opening 24, the researcher inserts the animal's head into restraining member 20 and clamps the animal behind the head with clamp 28, preventing animal 26 from withdrawing its head from restraining member 20. The operator then fits seal 22 onto the animal's head, sliding sealing member frame 30 onto restraining member 20. Sealing member frame 30 slides over the top of clamp 28 to prevent movement of clamp 28 from around the animal's neck. Finally, the operator inserts the combined sealing member 18 and restraining member 20, and the restrained animal 26, into thoracic chamber 12, positioning sealing member 18 adjacent interface 16 between chambers 12 and 14.

Restraining member 20, illustrated in exploded view in FIG. 2, preferably includes a cylindrical wall section 38 sized so that a peripheral flange at the rear of the sealing member frame 30 can be frictionally fitted over the forward end of wall section 38. Clamp 28 is inserted through slot 40 in wall section 38. Restraining member 20, in the preferred embodiment, also includes a body platform 42 to support the animal's body while the animal's head is held by clamp 28. Frame 30, when inserted onto the end of restraining member 20 is positioned over slot 40 to prevent removal of clamp 28 during use.

In the embodiment illustrated in FIGS. 1-3, clamp 28 is a plate having a U-shaped opening 44 formed by two spaced, parallel tines 46, which may be joined by a handle section 48. In use, clamp 28 is inserted through slot 40 in restraining member 20, with tines 46 being positioned on opposite sides of the animal's neck.

Figure 6:
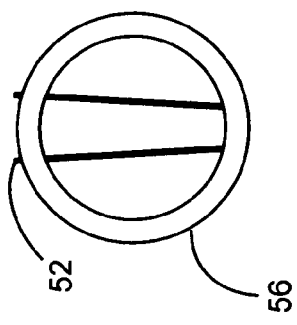
FIG. 6 is an end view of the restraining member of FIG. 4 with the clamping means in the closed position.
Figure 5:
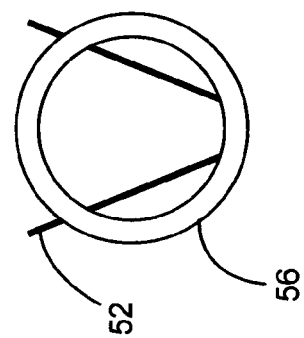
FIG. 5 is an end view of the restraining member of FIG. 4 with the clamping means in the open position.
Figure 4:
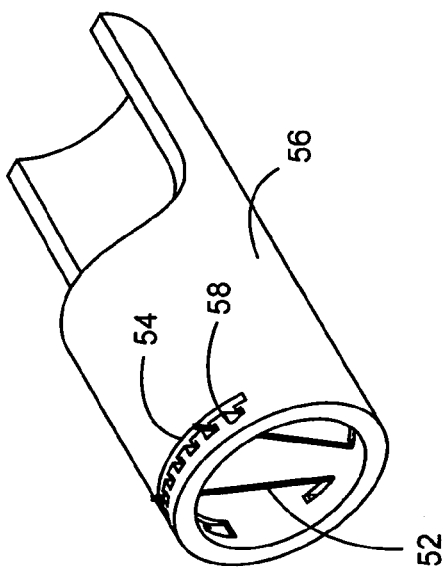
FIG. 4 is a perspective view of a restraining member with an alternative clamping means.

Alternative clamps will occur to one skilled in the art after reading the present description, the only requirement being that the clamp prevents the test animal from withdrawing its head from the restraining member without preventing the animal from breathing. For example the clamp illustrated in FIGS. 4-6 is comprised of a pair of spaced pivotal pins or rods 52 positioned in a plane transverse to the longitudinal axis of the restraining member opening. Pins 52 are pivotal between an open position and one or more selected closed positions. Slot 54 in restraining member 56 includes latching grooves 58 to hold pins 52 in the selected closed positions. In use, pins 52 are placed in their open position until the animal's head is inserted, and pivoted toward each other until withdrawal of the animal's head is prevented.

Figure 9:
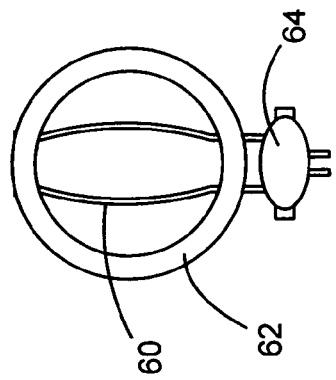
FIG. 9 is an end view of the restraining member of FIG. 7 with the clamping means in the closed position.
Figure 8:
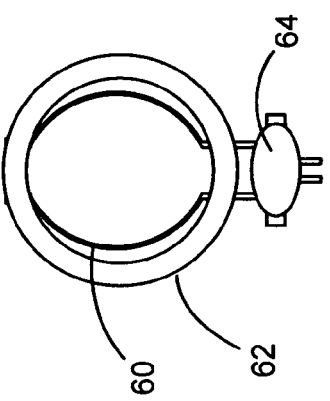
FIG. 8 is an end view of the restraining member of FIG. 7 with the clamping means in the open position.
Figure 7:
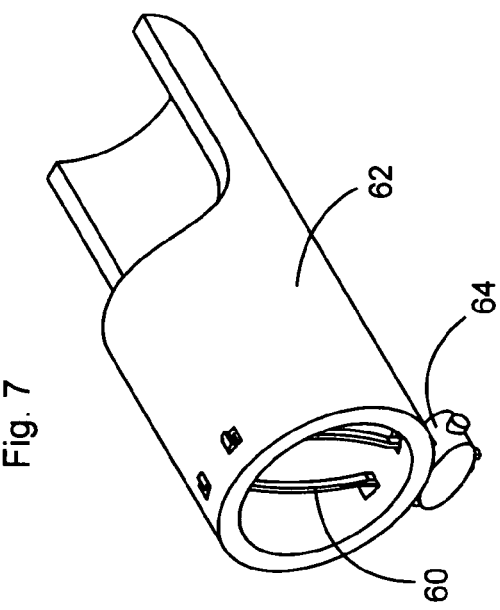
FIG. 7 is a perspective view of a restraining member with another alternative clamping means.

In a third embodiment, illustrated in FIGS. 7-9, spaced flexible cords 60 extend across the interior of restraining member 62. When in their open or relaxed state, cords 60 permit the animal to insert its head into restraining member 62. However, when cords 60 are tightened, e.g., by pulling cords 60 taut with cord lock 64, the spacing between the cords prevents the animal from withdrawing its head.

Other components conventional to plethysmographs may be included. For example, as shown in FIG. 3, the plethysmograph includes ports 66 for communication with a pressure transducer (not shown) to measure air within the interior of chambers 12 and 14. Manifold 68, as described in detail in U.S. Pat. No. 6,902,532, incorporated herein by references in its entirety, provide air via pneumotachs (not shown) and conduits 70 and 72 to chambers 12 and 14, respectively, and to reference chambers 74 and 76, respectively. A closable inlet 78 is used to add aerosol to chamber 14. Manifolds 80 and 82 communicate with chambers 12 and 14 for bias flow.

Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A duel-chamber plethysmograph for transmitted test animal pulmonary data to differential pressure transducers comprised of:
   a) a first chamber having a first attachment opening;
   b) a second chamber having a second attachment opening attachable to said first attachment opening at an interface;
   c) a sealing member insertable into said plethysmograph between said first and second chambers to block the passage of air between said chambers, said sealing member including a seal with an opening to receive the head of the test animal whereby the animal breaths air in the second chamber, while the animal's body is within the first chamber; and
   d) a restraining member attachable to said sealing member, said restraining member including a clamp positionable behind the test animal's head, thereby preventing the animal from withdrawing its head from the restraining member, said restraining member and said sealing member being insertable into said second chamber after the test animal is placed in said restraining member and held by said clamp.

2. The plethysmograph of claim 1, wherein said restraining member includes a continuous wall surrounding the area into which the test animal's neck is positioned, said wall including a slot for insertion of said clamp.

3. The plethysmograph of claim 1, wherein said restraining member includes a platform to support the animal's body.

4. The plethysmograph of claim 1, wherein said clamp is comprised of a pair of spaced clamping pins pivotal between an open position permitting insertion of the animal's head and selected clamped position preventing withdrawal of the animal's head, said restraining member including latching means to secure said pins at said selected clamping positions.

5. The plethysmograph of claim 1, wherein said restraining member includes a continuous wall section surrounding the area into which the test animal's neck is positioned, and said clamp is comprised of a pair of spaced cords extending across said wall section, said cords having a relaxed position permitting insertion of the animal's head and a taut position preventing withdrawal of the animal's head.

6. The plethysmograph of claim 1, wherein said chamber are cylindrical and said sealing member is circular with an O-ring about its periphery frictionally engaging one the chambers when inserted into said plethysmograph.

7. The plethysmograph of claim 1, wherein said seal is an annular flexible seal with central opening.

8. The plethysmograph of claim 1, wherein so sealing member is frictionally attachable to said restraining member.

9. A dual-chamber plethysmograph for transmitted test animal pulmonary data to a differential pressure transducer comprised of:
   a) a cylindrical first chamber having a first attachment end;
   b) a cylindrical second chamber having a second attachment end attachable to said first attachment end;
   c) a sealing member to block the passage of air between said chambers, said sealing member including a circular frame having an O-ring about its periphery, and a seal extending across said frame, said seal having an opening to receive the head of the test animal, whereby the animal breaths air in the second chamber, while the animal's body is within the first chamber; and d) a restraining member attachable to said sealing member, said restraining member including a clamp positionable behind the test animal's head, thereby preventing the animal from withdrawing its head from the restraining member, said restraining member and said sealing member being insertable into said chamber after the test animal is placed in said restraining member and held by said clamp.

10. The plethysmograph of claim 9, wherein said restraining member includes a platform to support the animal's body.

11. The plethysmograph of claim 9, wherein said clamp is the only component of said plethysmograph preventing the animal from withdrawing its head from the seal during use of the plethysmograph.

12. The plethysmograph of claim 9, wherein said clamp has a U-shaped neck-receiving opening.

13. The plethysmograph of claim 9, wherein said clamp is comprised of a pair of spaced clamping pins pivotal between an open position permitting insertion of the animal's head and a clamped position preventing withdrawal of the animal's head.

14. The plethysmograph of claim 9, wherein said clamp is comprised of a pair of spaced flexible cords having a relaxed position permitting insertion of the animal's head and taut position preventing withdrawal of the animal's head.

* * * * *